(12) United States Patent
Murdock

(10) Patent No.: US 9,802,129 B2
(45) Date of Patent: Oct. 31, 2017

(54) INTERNET SPORTS COMPUTER CELLULAR DEVICE

(76) Inventor: Wilbert Q. Murdock, Bronx, NY (US)

( * ) Notice: Subject to any disclaimer, the term of this patent is extended or adjusted under 35 U.S.C. 154(b) by 1389 days.

(21) Appl. No.: 11/901,552

(22) Filed: Sep. 18, 2007

(65) Prior Publication Data
US 2008/0188310 A1 Aug. 7, 2008

Related U.S. Application Data

(63) Continuation-in-part of application No. 09/570,233, filed on May 12, 2000, now Pat. No. 7,789,742.

(51) Int. Cl.
*A63B 69/36* (2006.01)
*A63F 13/92* (2014.01)
(Continued)

(52) U.S. Cl.
CPC .............. *A63F 13/92* (2014.09); *A63B 69/00* (2013.01); *A63B 69/3632* (2013.01); *A63F 13/00* (2013.01); *A63F 13/34* (2014.09); *A61B 5/00* (2013.01); *A63B 24/0075* (2013.01); *A63B 69/26* (2013.01); *A63B 69/38* (2013.01); *A63B 2069/0008* (2013.01); *A63B 2071/063* (2013.01); *A63B 2102/02* (2015.10); *A63B 2102/18* (2015.10); *A63B 2102/32* (2015.10); *A63B 2220/12* (2013.01); *A63B 2220/40* (2013.01); *A63B 2225/20* (2013.01); *A63B 2225/50* (2013.01); *A63B 2230/04* (2013.01); *A63B 2230/06* (2013.01); *A63B 2230/10* (2013.01); *A63B 2230/42* (2013.01);
(Continued)

(58) Field of Classification Search
CPC ... A61B 5/00; A63B 2220/40; A63B 2220/50; A63B 69/3632
See application file for complete search history.

(56) References Cited

U.S. PATENT DOCUMENTS 5,099,702 A * 3/1992 French ................ A61B 5/1036
273/454
5,447,305 A * 9/1995 Socci ................... A42B 3/0433
473/458

(Continued)

*Primary Examiner* — William H McCulloch, Jr.

(57) ABSTRACT

A system that wirelessly integrates actual sports equipment with a computer and the internet to allow players remotely located from one another to play a competitive simulated sports game. An individual player may opt to play solo or practice to improve basic techniques. The system includes motion sensors connected to the player and a motion sensing device, all containing circuits and contact or motion sensors coupled with signal processing and radio frequency transmitter circuitry, thereby wirelessly communicate game performance information to a remote receiver-computer. The computer displays player information and visually simulates and controls a game between two players via the internet, having similar equipment and remotely located from each other. Standard sports equipment may be retrofitted with the sensors and associated circuitry to convert such equipment into "smart equipment" for use with the system. The system employs specially developed computer software to process player performance data, control game play, communicate game information between players, generate and control visual simulations and display player performance information.

13 Claims, 16 Drawing Sheets

SIMPLE FLOWCHART OF MEGA MACHINE

Figure 1:
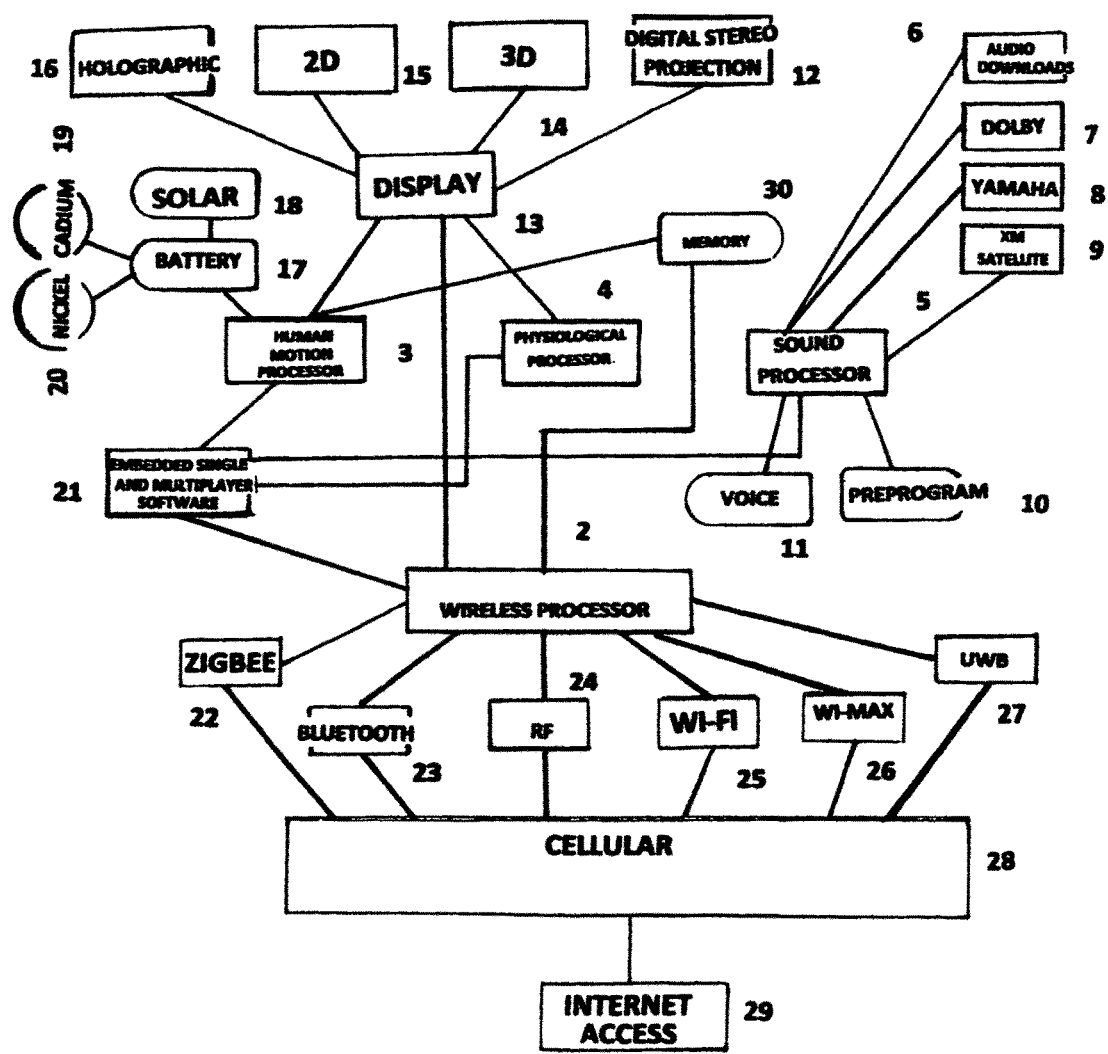

(51) Int. Cl.
   *A63F 13/34*    (2014.01)
   *A63B 69/00*    (2006.01)
   *A63F 13/00*    (2014.01)
   *A63F 13/332*   (2014.01)
   *A63F 13/327*   (2014.01)
   *A63F 13/816*   (2014.01)
   *A63F 13/216*   (2014.01)
   *A63F 13/87*    (2014.01)
   *A61B 5/00*     (2006.01)
   *A63B 24/00*    (2006.01)
   *A63B 69/26*    (2006.01)
   *A63B 69/38*    (2006.01)
   *A63B 71/06*    (2006.01)
   *A63B 102/32*   (2015.01)
   *A63B 102/02*   (2015.01)
   *A63B 102/18*   (2015.01)

(52) U.S. Cl.
   CPC . *A63B 2243/0037* (2013.01); *A63B 2244/102* (2013.01); *A63F 13/216* (2014.09); *A63F 13/327* (2014.09); *A63F 13/332* (2014.09); *A63F 13/816* (2014.09); *A63F 13/87* (2014.09); *A63F 2300/105* (2013.01); *A63F 2300/204* (2013.01); *A63F 2300/407* (2013.01); *A63F 2300/6607* (2013.01); *A63F 2300/8011* (2013.01)

(56) References Cited

U.S. PATENT DOCUMENTS

| | | | | |
|---|---|---|---|---|
| 5,592,401 A * | 1/1997 | Kramer | A63B 69/3608 | 340/524 |
| 6,013,007 A * | 1/2000 | Root | A63B 24/0006 | 482/8 |
| 6,018,705 A * | 1/2000 | Gaudet | A61B 5/1121 | 235/105 |
| 6,148,271 A * | 11/2000 | Marinelli | A63B 43/00 | 473/198 |
| 6,157,898 A * | 12/2000 | Marinelli | A63B 43/00 | 473/569 |
| 6,842,877 B2 * | 1/2005 | Robarts | G06F 1/163 | 700/65 |
| 7,055,101 B2 * | 5/2006 | Abbott | G06F 1/163 | 706/45 |
| 7,499,828 B2 * | 3/2009 | Barton | A63B 24/0003 | 473/220 |
| 7,607,243 B2 * | 10/2009 | Berner, Jr. | A43B 3/0005 | 36/136 |
| 7,625,314 B2 * | 12/2009 | Ungari | A63B 69/0053 | 482/1 |
| 7,789,742 B1 * | 9/2010 | Murdock | A63B 24/0021 | 273/108 |
| 7,821,407 B2 * | 10/2010 | Shears | A61B 5/1127 | 340/573.1 |
| 7,837,572 B2 * | 11/2010 | Bissonnette | A63B 24/0003 | 273/317.2 |
| 7,969,315 B1 * | 6/2011 | Ross | A43B 3/0005 | 340/539.11 |
| 8,015,732 B2 * | 9/2011 | Berner, Jr. | A43B 3/0005 | 36/136 |
| 8,033,996 B2 * | 10/2011 | Behar | A61B 5/0002 | 128/920 |
| 8,052,539 B2 * | 11/2011 | Kimber | A63B 69/3632 | 473/222 |
| 8,360,904 B2 * | 1/2013 | Oleson | A63B 24/0062 | 463/36 |
| 8,493,822 B2 * | 7/2013 | Lee | A63B 71/0686 | 369/30.09 |
| 8,952,796 B1 * | 2/2015 | Wolf | G06F 3/016 | 340/407.1 |
| 8,989,835 B2 * | 3/2015 | Badower | A61B 5/00 | 600/383 |
| 9,369,365 B2 * | 6/2016 | Molettiere | H04L 67/22 |  |
| 9,381,420 B2 * | 7/2016 | Burroughs | G06F 19/3481 |  |
| 9,389,057 B2 * | 7/2016 | Meschter | G06F 19/3406 |  |
| 9,403,060 B2 * | 8/2016 | Molyneux | A43B 1/0054 |  |
| 9,456,785 B1 * | 10/2016 | Matak | H04Q 9/00 |  |
| 9,549,585 B2 * | 1/2017 | Amos | G01C 22/006 |  |
| 2002/0077189 A1 * | 6/2002 | Tuer | A63B 69/3632 | 473/151 |
| 2002/0083025 A1 * | 6/2002 | Robarts | G06F 1/163 | 706/12 |
| 2002/0116147 A1 * | 8/2002 | Vock | A63C 5/06 | 702/182 |
| 2002/0123386 A1 * | 9/2002 | Perlmutter | A63B 24/0021 | 473/223 |
| 2003/0149349 A1 * | 8/2003 | Jensen | A61B 5/02055 | 600/372 |
| 2004/0033843 A1 * | 2/2004 | Miller, IV | A63B 24/0003 | 473/274 |
| 2004/0046692 A1 * | 3/2004 | Robson | A63B 24/0021 | 342/357.57 |
| 2004/0259651 A1 * | 12/2004 | Storek | A63B 69/3632 | 473/131 |
| 2006/0136173 A1 * | 6/2006 | Case, Jr. | A63B 24/00 | 702/182 |
| 2007/0260421 A1 * | 11/2007 | Berner, Jr. | A43B 3/0005 | 702/160 |
| 2008/0188310 A1 * | 8/2008 | Murdock | A63F 13/00 | 463/42 |

* cited by examiner

FIGURE 1-SIMPLE FLOWCHART OF MEGA MACHINE

MEGA MACHINE

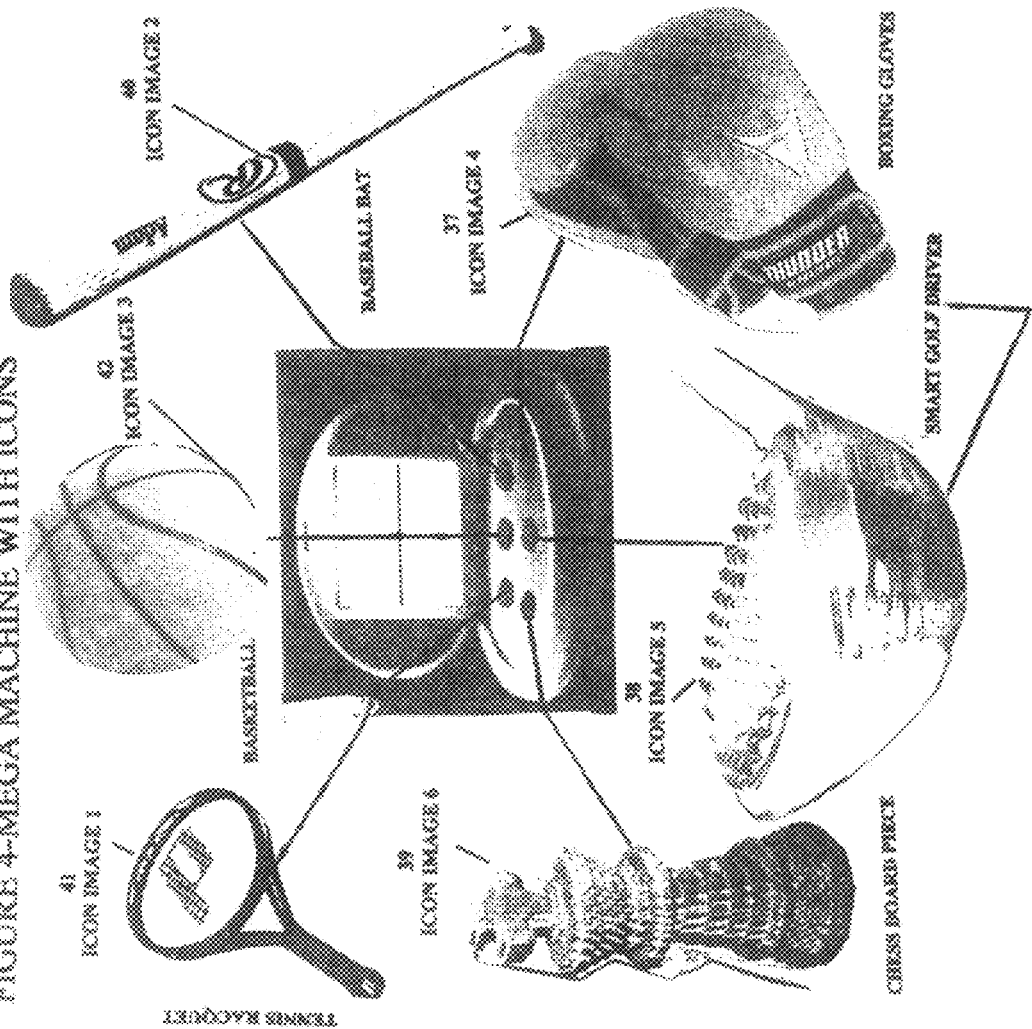

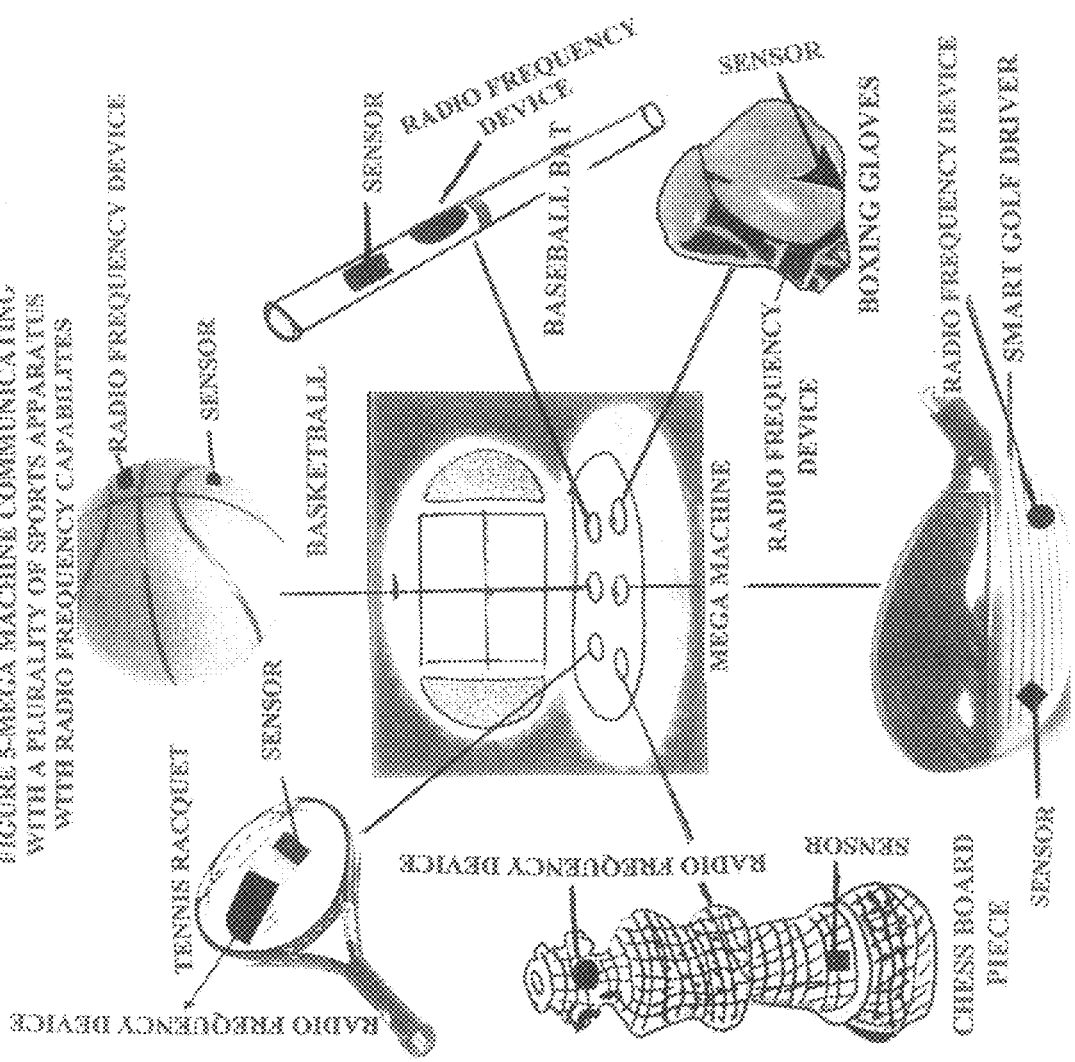

FIGURE 6-INFRARED MARKER AND STICK FIGURE OF LOWER EXTREMITY
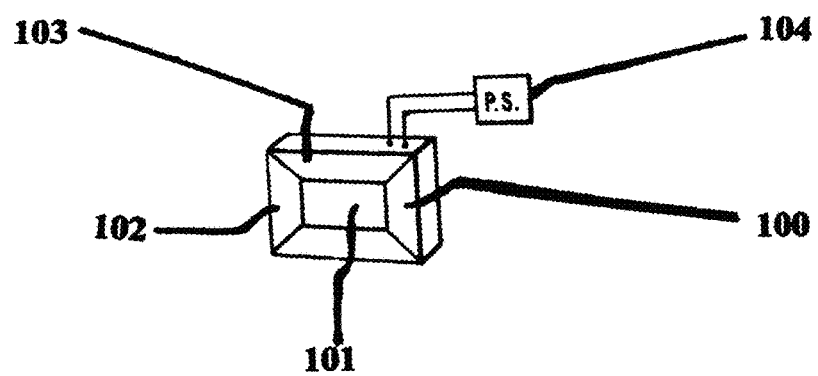
INFRARED MARKER
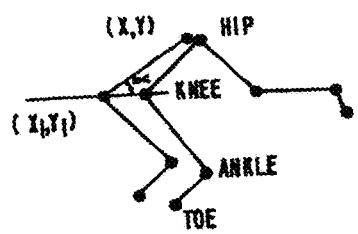
REAL-TIME STICK FIGURE OF LOWER EXTREMITY

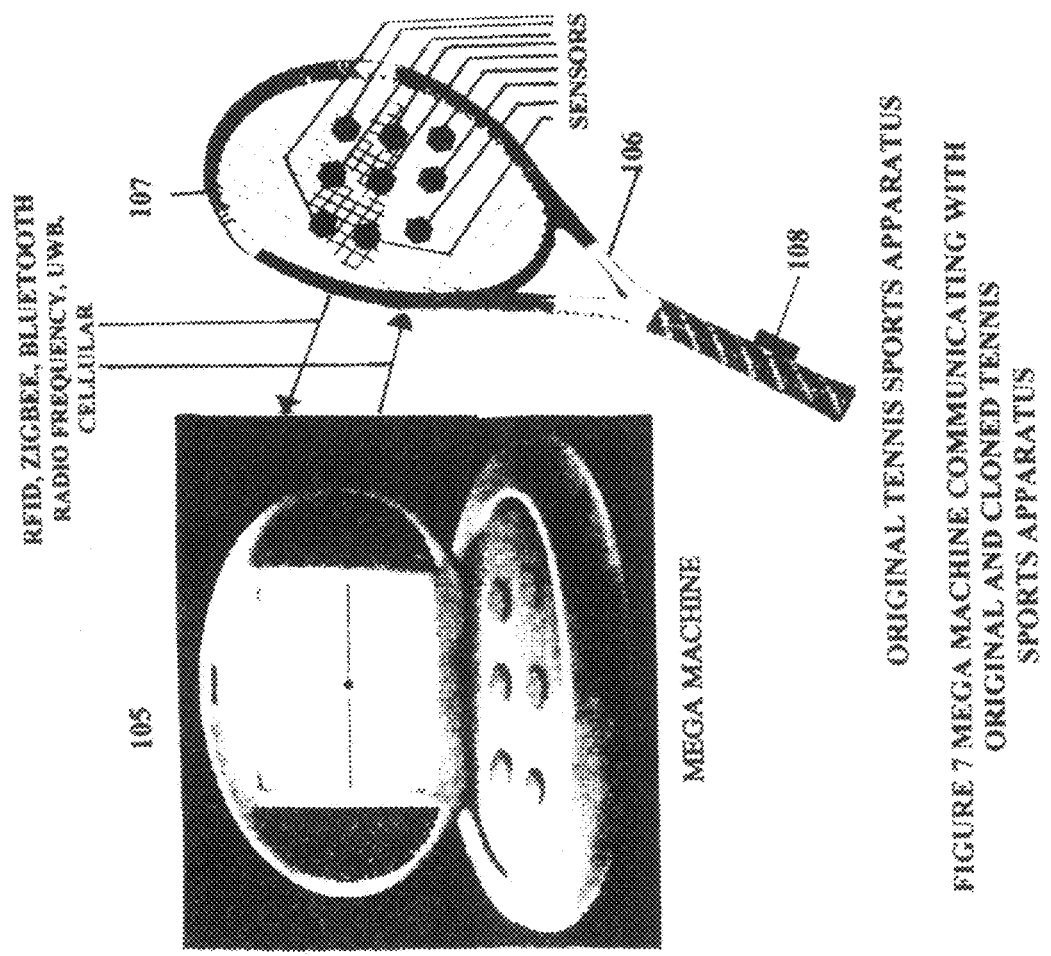

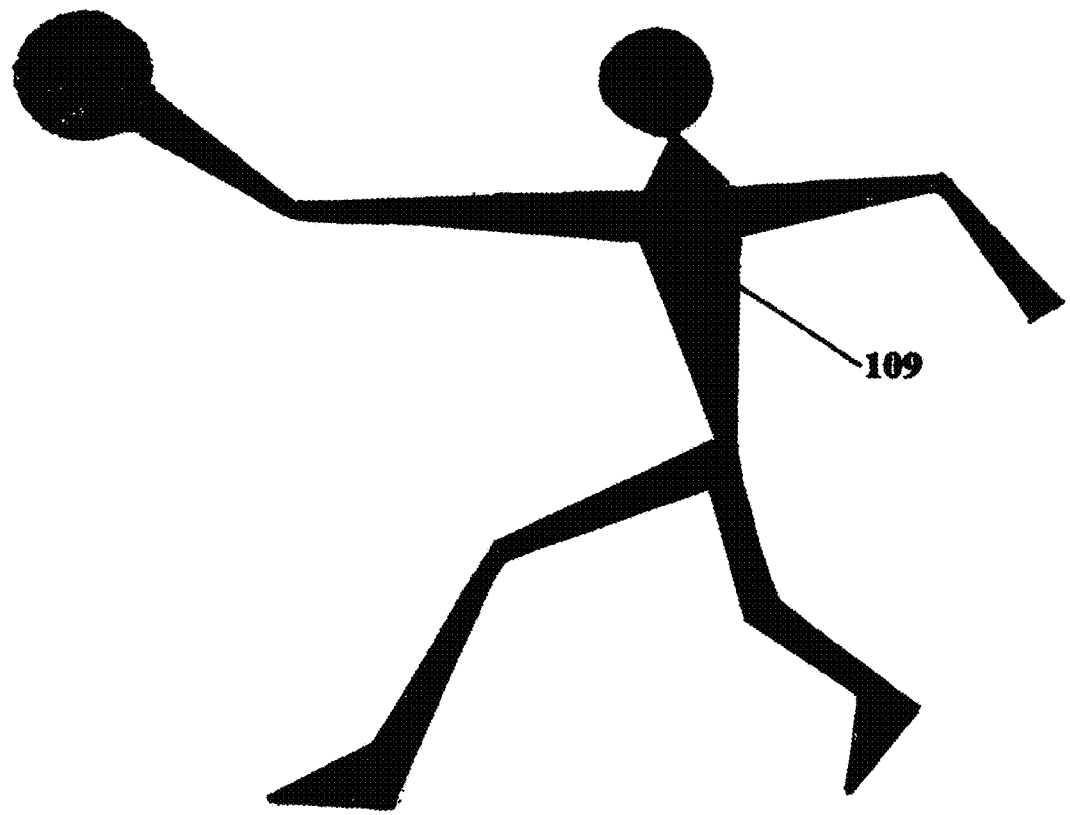
FIGURE 8 MEGA MACHINE GENERATED REAL-TIME STICK FIGURE

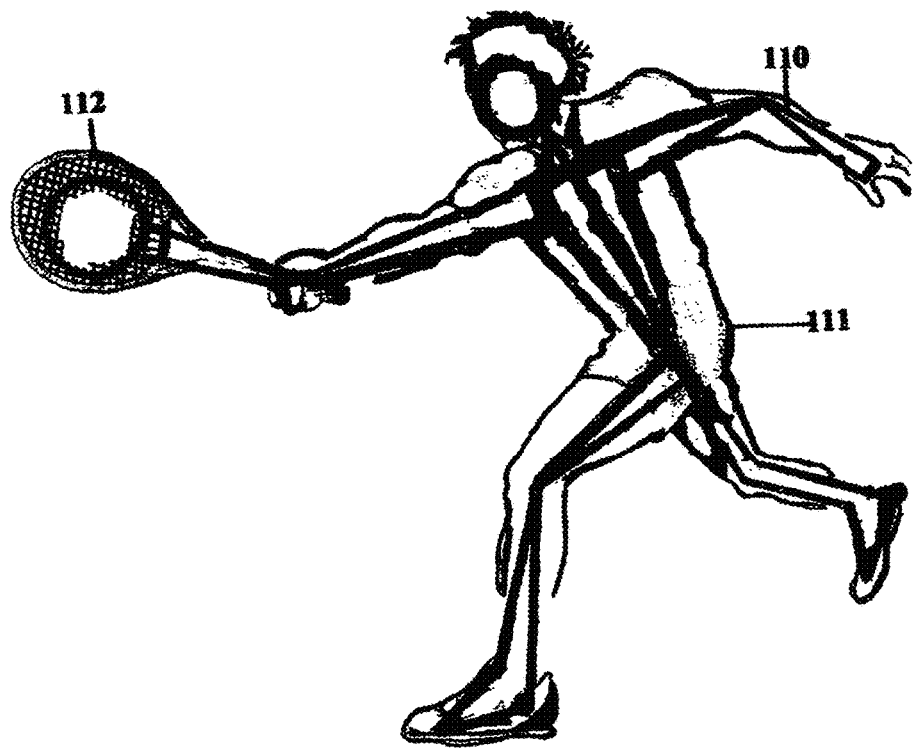
FIGURE 9 MEGA MACHINE GENERATED REAL-TIME FIGURE SUPERIMPOSED OVER VIDEO IMAGE

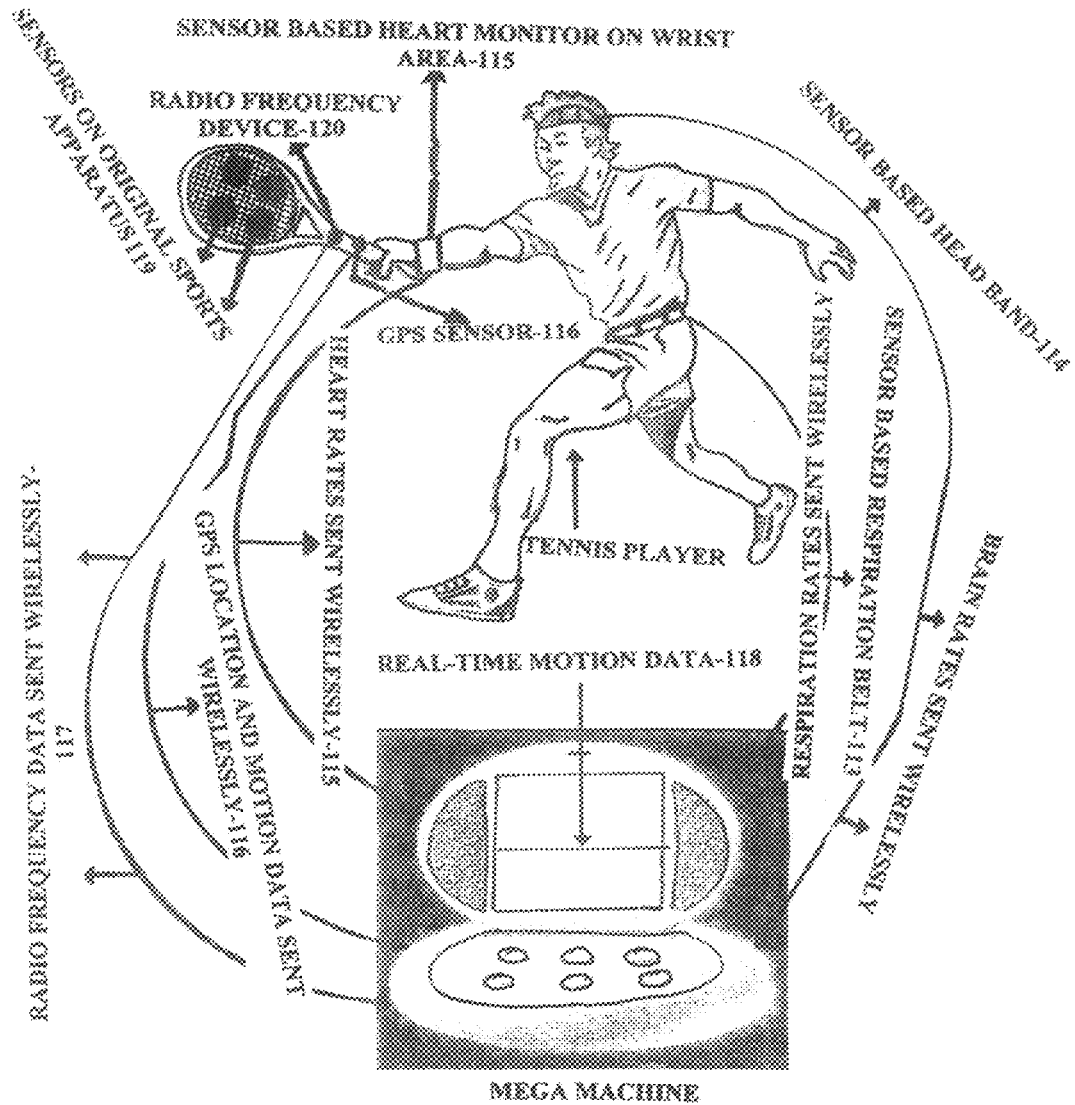
FIGURE 10-MULTIPLE STREAMS OF DATA BEING FEED INTO A MEGA MACHINE IN REAL-TIME

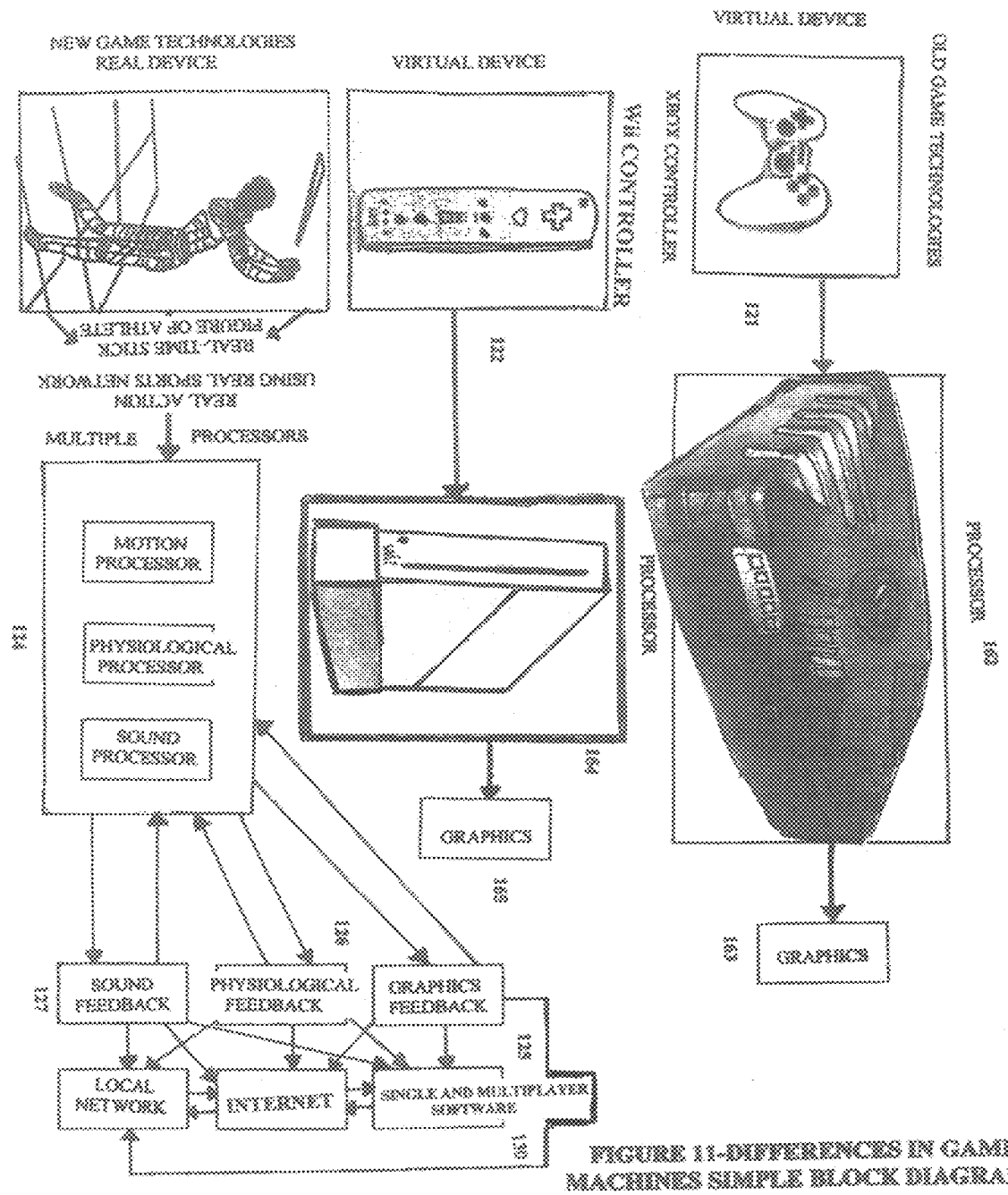

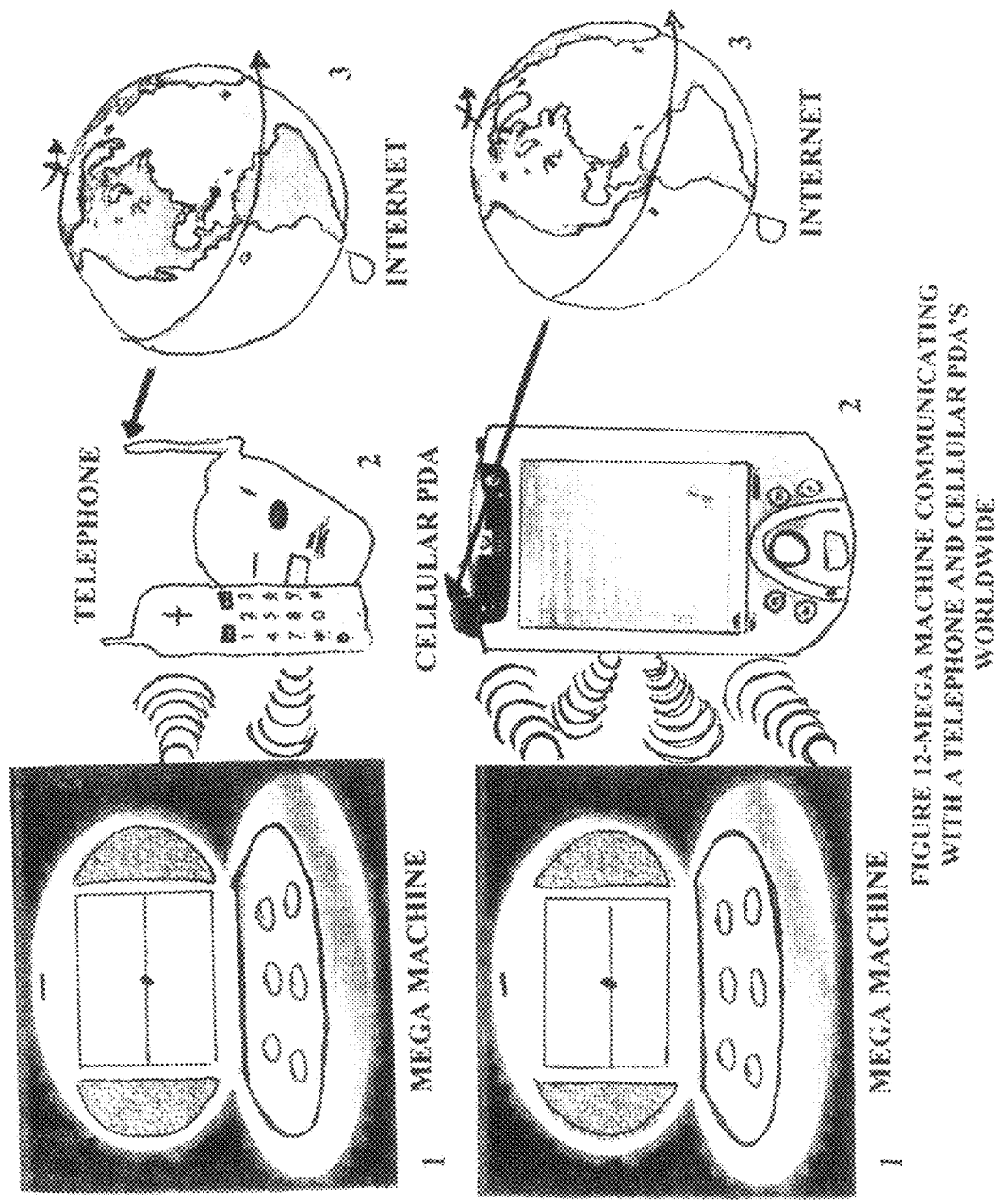

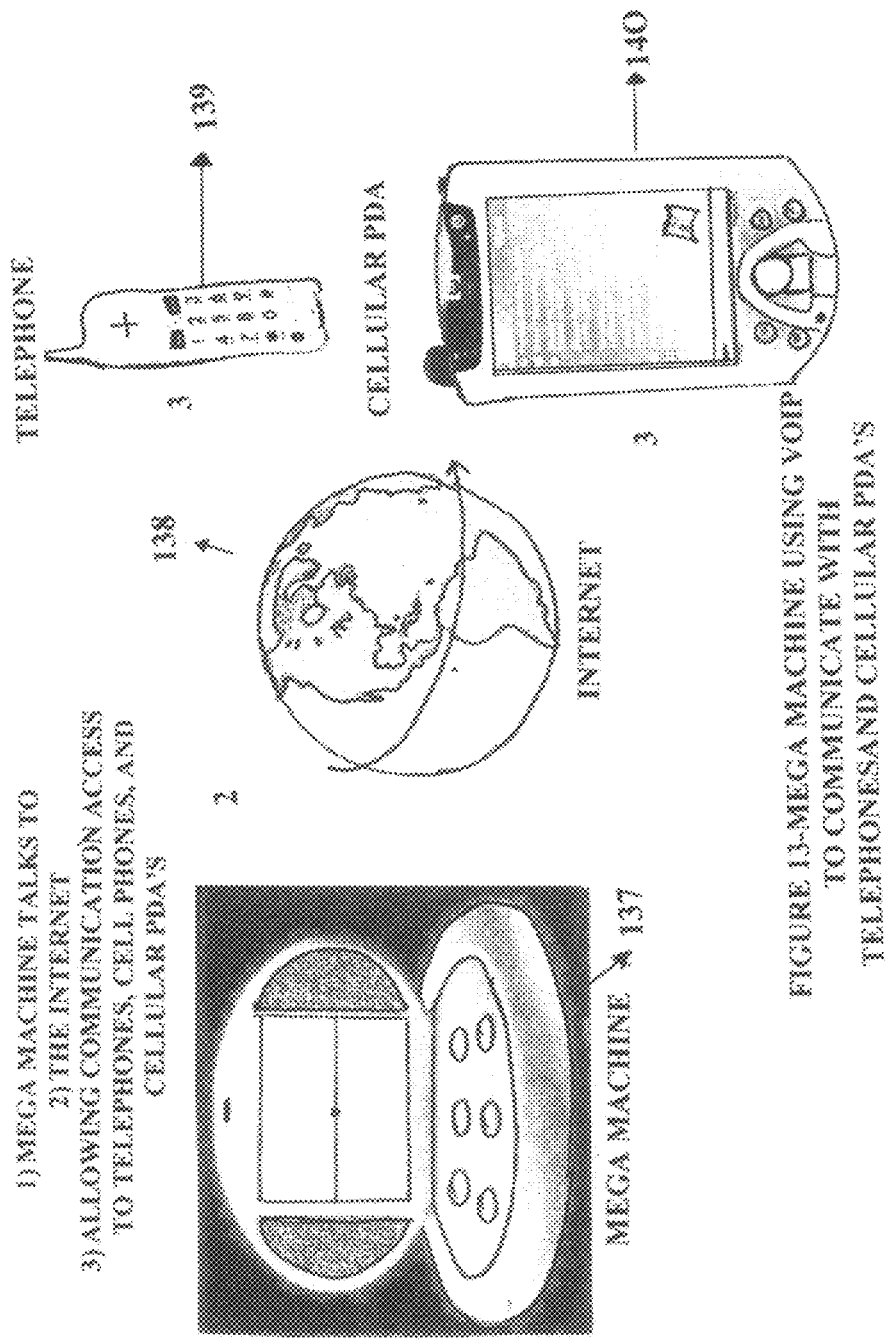

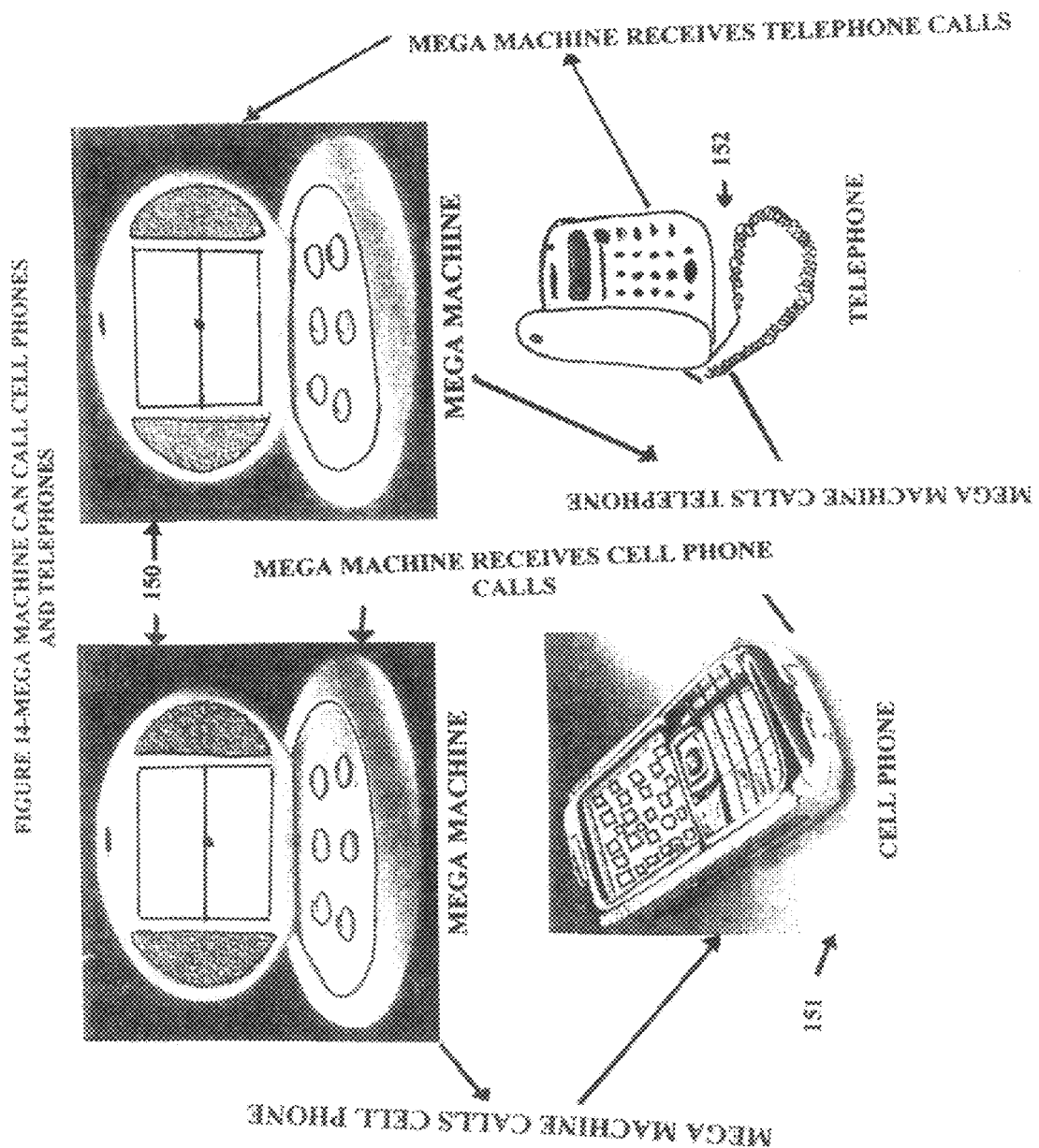

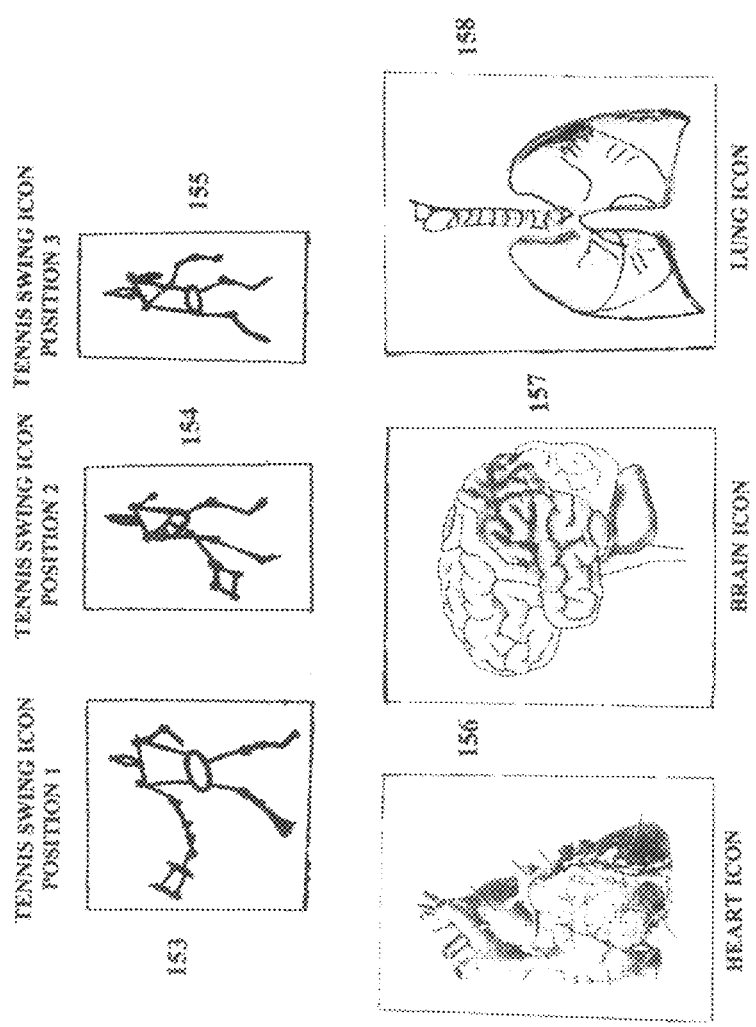

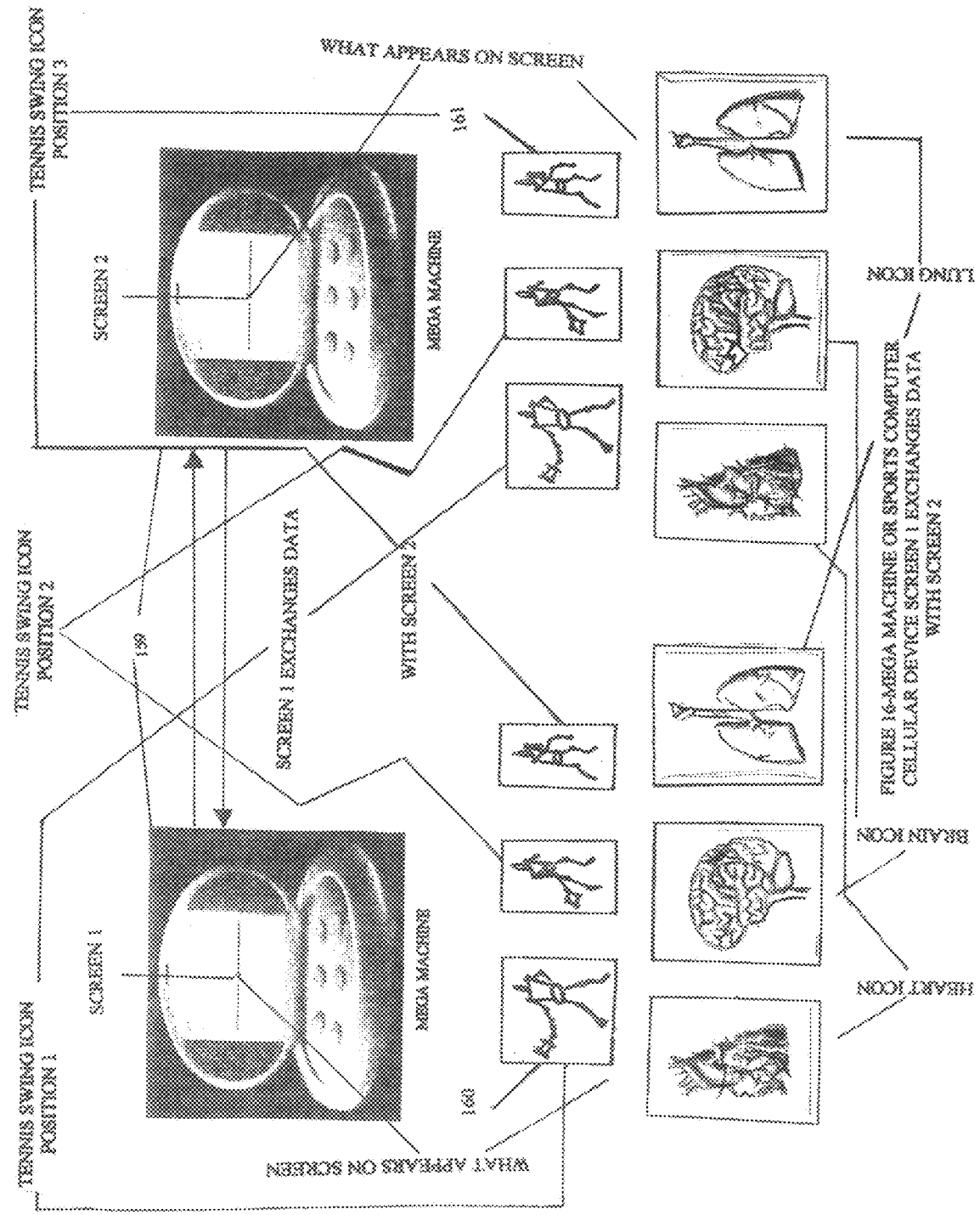

INTERNET SPORTS COMPUTER CELLULAR DEVICE

PRIORITY CLAIM

This application is a continuation-in-part of U.S. patent application Ser. No. 09/570,233, filed May 12, 2000, which, in turn, claims the benefit and priority of U.S. Provisional patent application 60/13722, filed May 12, 1999. The above referenced applications are incorporated herein by reference as if restated in full.

FIELD OF THE INVENTION

This invention relates to a system coupling actual sporting equipment and a computer.

BACKGROUND OF THE INVENTION

A number of patented interactive sports simulation devices embody various athletic motion sensing components. Typically, these devices display information related to a player's movements. In certain of these, the information is displayed or signaled by some part of the player or sports equipment itself in the form of a small visual readout or an audible sound. For example, one such device contains an array of mechanically depressible pins on the face of the golf club. When the ball is struck by the club, the pins are physically depressed in a pattern to inform the player of the location on the club face where contact with the ball occurred. Another device uses a light emission and reflection detection technique to provide a player information, displayed on the equipment, regarding the alignment of the equipment with the preferred location on the particular equipment.

Also, numerous conventional computer software packages and video games use a variety of unrealistic techniques to emulate sports-specific motions.

It is desirable to remotely communicate actual player performance information, whereby more sophisticated analysis and prediction possibilities are realizable via computer technology and state of the art display techniques. Further, it is also desirable to use such performance information in an expanded capacity to provide interactive competitive play among numerous players in locations remote from each other.

Most game machines rely on the same principles which are usually using the fastest central processing unit, the best graphics chip, and a host of technical innovations that give the garners more control over their game action.

A number of gaming devices in the market today call for the need to develop a motion processor which allows gamers and athletes to become an integral part of the action. These devices still lack complete interactivity, which the present invention now brings to reality.

Figure 2:
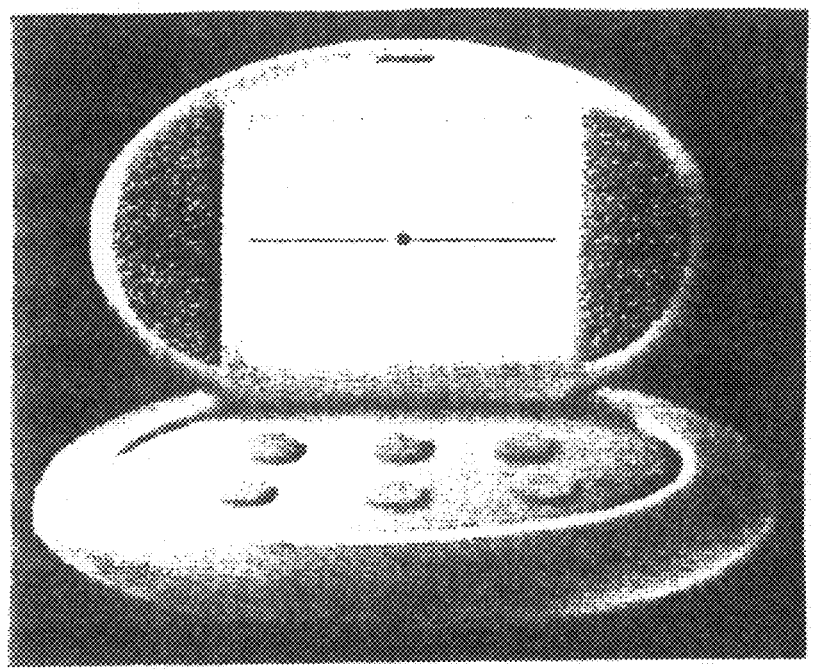
Figure 3:
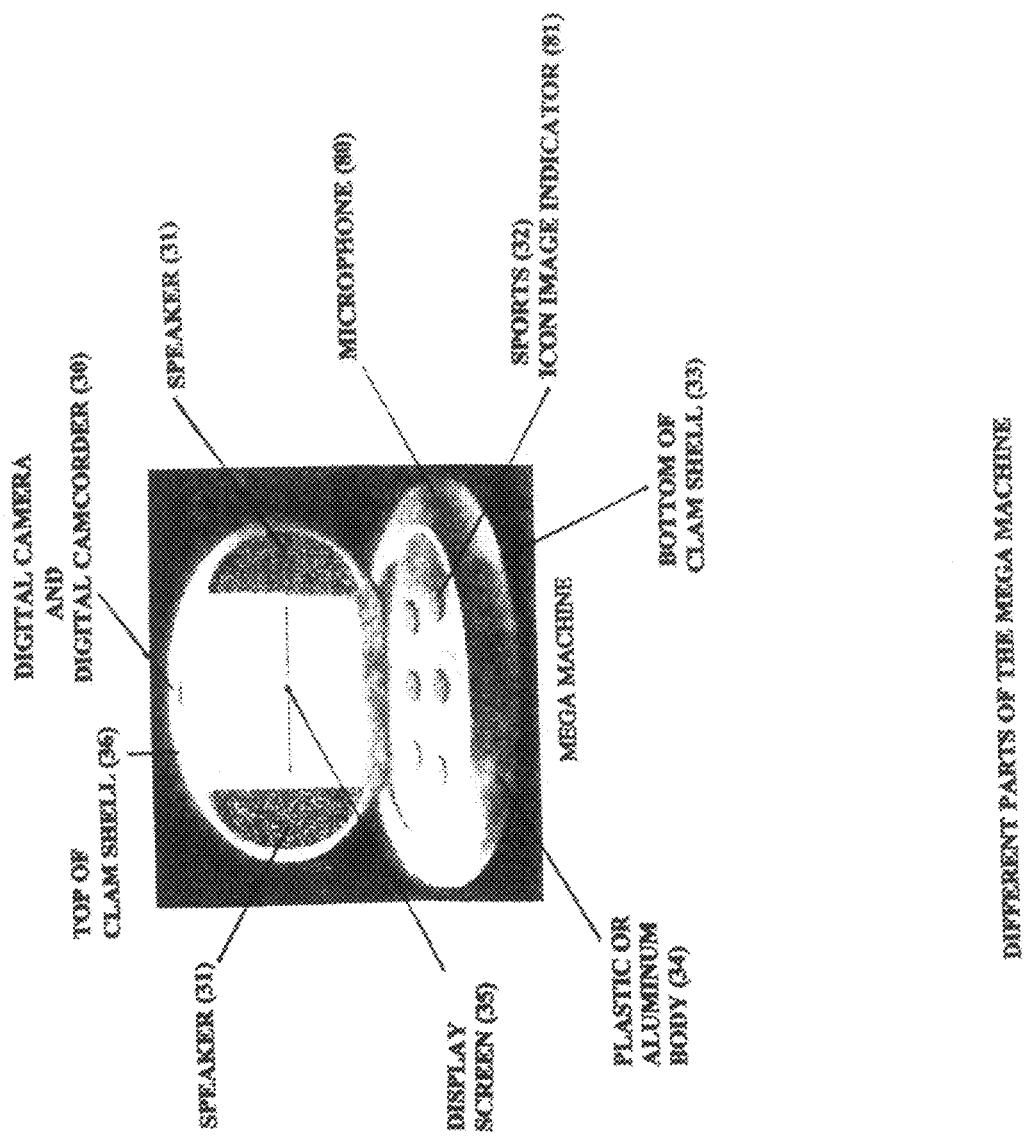

FIG. 1 shows a flowchart of an exemplary system.
FIG. 2 shows an exemplary embodiment of the invention.
FIG. 3 shows an exemplary embodiment of the invention.
FIG. 4 shows an exemplary embodiment of the invention.
FIG. 5 shows an exemplary embodiment of the invention.
FIG. 6 shows an exemplary embodiment of the invention.
FIG. 7 shows an exemplary embodiment of the invention.
FIG. 8 shows an exemplary animation produced by an embodiment of the invention.
FIG. 9 shows an exemplary animation produced by an embodiment of the invention.
FIG. 10 shows an exemplary embodiment of the invention.
FIG. 11 shows an exemplary embodiment of the invention.
FIG. 12 shows an exemplary embodiment of the invention.
FIG. 13 shows an exemplary embodiment of the invention.
FIG. 14 shows an exemplary set of communication mediums of embodiment of the invention.
FIG. 15 shows an exemplary set of icons for an embodiment of the invention.
FIG. 16 shows an exemplary set of icons for an embodiment of the invention.

BRIEF DESCRIPTION OF THE INVENTION

This invention relates to a system that interconnects real sports equipment to a computer. In a preferred embodiment the computer is coupled wirelessly to a user, sports equipment, a receptacle, or a sport-specific motion sensing component. Further, the invention, with the components summarized below, allows one or more players to enter into a competition against each other. Each player asks the computer who is available to play a contest. Once a player pairs up against another player anywhere in the world and play ensues, the computer and display show each participant's score via animation or graphics that preferably relate to a player's individual performance statistics. A single player may play without an opponent to practice and improve basic sport-specific skills using the computer and display to track performance. In an advantageous embodiment the present invention accomplishes this through a continuous process wherein the present invention establishes a plane of space, reads how the player moves his or her body within said plane of space, and determines the optimized levels of performance based on the player's age, body type, playing style, and years of experience, which are inputted into the system. All of this information can be transferred to a server by a client, minimizing the required storage of information on the unit itself.

The system application is unlimited. Much of this system can be used not only for golfing competition on the Internet, but for other sports as well. Sports implements other than golf clubs, swing detectors and receptacles can be outfitted with sensors according to this invention and used for training purposes, rehab, or for interactive internet competition. The technology can be used for training, competition, and the improvement of player reflexes and coordination. With little or no modification, the technology also has applications in medicine, particularly physical therapy.

A wireless piece of sporting equipment is constructed to contain, or alternatively a standard piece of sporting equipment is modified to contain, a multiple sensor or transducer array located on the surface of said equipment.

In one embodiment, the sporting equipment is a tennis racket, coupled with a tennis ball. Upon impact of the racket with a tennis ball, the impacted sensors produce detectable variances representing the magnitude and duration of the racket-ball impact force and the proximate location of such contact relative to the preferred location, the "sweet spot", on the face of the racket. The variances are electronically processed into digitally coded information and remotely transmitted by an electrical communication circuit either contained within or attached to the tennis racket.

A ball receiver may be a receptacle with an open end to receive a ball and contains a transducer located so as to sense the ball entering receptacle. Upon impact with the ball, the sensor produces a detectable variance representing impact with the ball. The variance is electronically processed into digitally coded information and remotely transmitted by an electrical communication circuit. In one preferred embodiment the communication circuit is contained within the receptacle. The communication circuit for the receptacle may be a radio frequency transmitter. The receptacle can either be designed for indoor use or can be a cup in an actual green with the communication circuit housed in the cup or elsewhere.

In a preferred embodiment, a sporting equipment device and ball receiving device contains transducers which are or include piezoactive elements. As used herein, "piezoactive" includes piezoelectric and piezoresistive components. Piezoactive components are defined as components the electrical properties of which, when the component is subjected to physical force, vary.

A motion sensing device contains an array of uniformly distributed sensing transducers upon or proximate to the device surface. This motion sensing device may be a camera. In a preferred embodiment, the surface is a clam-shaped handheld device. The camera produces detectable varying characteristics representing the velocity, angle, and proximity of a user and or a piece sporting equipment relative to the surface of the device. The variances are electronically processed into digitally coded information and remotely transmitted by an electrical communication circuit contained within or electronically connected to the device.

At each remote player site, wireless radio frequency equipment receives the digitally coded transmitted signals from the user and or a piece of sporting equipment, a ball receptacle, and the motion sensing device. The signals are demodulated and processed into serial binary data suitable for communications to the computer via either serial or parallel ports. As the game progresses, the computer under the control of the software monitors and directs the flow of communications between the players via the internet and displays the game simulations and performance information.

At each remote player site, a computer under the control of the software program monitors and controls the sequential play of the game and interacts with the player at the site and also competing players at other remote sites via the internet. The software system generates the game simulations for display and tracks each player's performance as the game progresses.

The above and further features and advantages of the invention will be better understood with reference to the accompanying drawings and the following detailed description of an exemplary embodiment.

DETAILED DESCRIPTION OF THE INVENTION

A preferred embodiment of the invention includes a wireless piece of sporting equipment, a wireless golf ball receptacle, a wireless golf club motion sensing plate, a wireless receiver connected to a computer, and a display or monitor with speakers operated under the control of system software, and connected via the internet to an internet game server.

1. Sport Specific Tool

The sport specific tool has a plurality of embedded contact sensors and internal electronic circuitry including a wireless radio frequency transmitter. At least one of the sensors is located at or proximate to the optimal location on a tool face for contact with any other sport specific tool, the "sweet spot". The remaining two sensors are adjacent and on either side of the sweet spot. The contact sensors may be, but are not limited to, sensors employing piezo-active type transducers, specifically, either piezo-electric or piezo-resistive transducers (similar, but not limited to the Cooper Instruments LPM 562).

In an alternative embodiment, three sensors are applied to the face of an adapted sport specific tool by a mylar tape or other means. Again, the electronic circuitry is internal to the sport specific tool and connects to the sensors by leads.

In another alternative embodiment, to retrofit a standard golf club, contact sensors are part of an adapter attached to an ordinary sport specific tool and wire connected to electronic circuitry attached to the club shaft or elsewhere on the sport specific tool.

In another embodiment, a ball contacting any sensor produces a detectable variance indicating the magnitude and duration of sensor-ball impact. The variance may be a change in resistance of a piezo-resistive transducer or a voltage change in the case of a piezo-electric transducer. The variance is detected and amplified by an associated amplifier and then is input to an associated integration circuit, the output of which represents the energy of the ball-club contact event. Connected to the integration circuit, a microprocessor is a multi-input channel signal processing circuit (similar, but not limited to a Motorola #68HC05) having analog to digital signal converting circuits (ADCs), one for each input channel, and a sequential digital signal encoding circuit connected so as to convert the ADC outputs into a time multiplexed serial digital data stream containing a binary coded word for each channel indicating the energy of the associated sensor-ball impact event.

A radio frequency transmitting circuit receives the serial digital data from the microprocessor and wirelessly transmits the information via an internal antenna to the receiver for subsequent processing by the computer.

2. Ball Receptacle

In another embodiment, a ball receptacle has a top shaped to allow entry of a ball. The receptacle has a contact sensor pad containing at least one contact sensor, a ball return mechanism, and internal electronic circuitry. The internal circuitry includes a wireless radio frequency transmitter. The preferred manifestation of this embodiment has contact sensor pad positioned within the receptacle such that the center activation area aligns with the center of a ball entry. Additional sensor activation areas are adjacent, one on either side of the center area. In the preferred embodiment, like the sensor used at the face of the club, the sensors may be, but are not limited to, sensors employing piezo-active type transducers, specifically, either piezo-electric or piezo-resistive transducers.

A ball entering the receptacle and contacting the sensor pad produces a detectable variance indicating the ball entry event. The variance may be a change in resistance in the case of a piezo-resistive transducer (similar, but not limited to Cooper Instruments LPM 562) or a voltage change in the case of a piezo-electric transducer. The variance is detected and amplified by an associated amplifier. This amplified signal then is input to a microprocessor having an analog to digital signal converting circuit (ADC) and a digital signal encoding circuit connected so as to convert the ADC output representing the sensors' signals into a serial digital data stream containing a binary coded word indicating the sensor-ball contact event. The microprocessor may be the same or similar to the microprocessor of the sport specific tool's electronics. A radio frequency transmitter circuit receives the serial digital data from the microprocessor and wirelessly transmits the information via an internal antenna to the receiver for subsequent processing by the computer.

The ball return mechanism can be as simple as a back plate located to be engaged by a golf ball entering the receptacle and supported and biased by a spring or springs to eject the ball. Other known ejection devices, similar to those used in pinball machines, and either mechanically or even electrically activated, can be used to improve the effect if desired.

The receptacle configuration is susceptible to much variation. The receptacle illustrated and described above is well suited to indoor use, on carpet for example. It is clear, however, that an actual cup, installed in an actual green, with real or synthetic grass, can be similarly equipped.

3. Motion Sensor Plate.

The motion sensor plate having a top motion plate and a bottom motion plate is used, wherein the top motion plate contains a plurality of capacitor-forming electrically isolated platelets (twelve platelets are illustrated in this exemplary preferred embodiment). They are evenly distributed at or just below the top plate's exterior upper surface. The bottom plate has a homogenous electrically conductive interior surface underlying the platelets. Each capacitive platelet contained in the top motion plate forms a capacitive component when the top and bottom motion plates are vertically closely spaced to form the golf club motion sensor plate. A suitable insulator may be sandwiched between the two plates. The structure is adhesively or otherwise mechanically joined and it may be covered or coated as desired. The result is a golf club motion sensor plate containing a capacitor matrix. The capacitive components are connected to form a capacitive network.

Applying an energizing high frequency alternating electrical signal having a frequency in the range from 100 MHz to 200 MHz from an oscillator to the golf club motion plate capacitive network produces a electromagnetic field above the surface of each platelet of the capacitive components of the motion sensor plate. Any object, including a golf club, passing near the surface of the energized motion plate will cause a perturbation of the electromagnetic field as illustrated by the sample possible pathways across the plate. A network of electrical comparator amplifiers is connected to the capacitor network. The comparator amplifiers of network are connected one to one with the capacitive elements of the capacitive network. The comparators of the network detect voltage variations occasioned by electromagnetic field disturbance due to a golf club moving over certain of the capacitive elements of the motion plate. Each different golf club motion over the energized motion plate will produce a uniquely identifiable signal from the comparator amplifier network. There are a variety of known proximity sensors that could be gathered together in an array like that of the platelets to serve as the transducer portion of the golf club motion detector.

The electrical signal from the comparative amplifier network is applied to an analog to digital signal converter (ADC) and the ADC digitized output signal is converted into a serial digital data stream by a multiplexer. This data identifies each platelet having had its field distrubed. The serial digital data can be input directly by wire from a multiplexer to the computer located at the site of the golf player and golf club motion sensor plate, or as in the preferred embodiment, the serial data can be transmitted to a remotely located receiver connected to the computer via a transmitter and an antenna included in the golf club motion electronic transmitter communication circuitry.

The computer, under the control of the golf system software, will analyze the serial digital club motion signal, recognize from the transmitted signals the platelets over which the club head passed and display the sport specific motion.

4. Wireless Signal Receiver and Computer.

At each player site, a wireless radio frequency signal receiver is connected to the computer by either the serial (USB) or parallel computer ports. The wireless signal receiver detects digitally coded radio frequency transmissions from the communication circuit associated with any of a smart sports equipment, a ball receptacle, or a motion sensing plate. The received transmissions are demodulated by the RF receiver circuitry connected to a microprocessor, which converts the demodulated data signal to serial binary coded data suitable for communications to a computer. The computer, under the control of the internally installed golf system software program, monitors and directs the flow of communications between remotely located players via the internet and displays the game simulations and performance information. In appropriate installations the wireless electromagnetic signals that communicate with the receiver may be infrared communications.

At each remote player site, the computer under the control of the software system program monitors and controls initialization and the sequential play of the game, or alternatively, the individual player practice session. Upon start up by a player at a particular site, the system input parameters are set and the system Internet and player data port interfaces are initialized as indicated. For Internet communications, the serial port of the computer is enabled in the preferred embodiment. A local player event listener is initialized. It will communicate events from one or more of the smart golf club, the golf ball receptacle and the motion sensor plate. The main operational software (program) thread is run, and the system awaits data input from the appropriate computer communications port.

If the competitive play mode has been selected, the program generates a player participation request and sends the request to the GGC game internet server (GGC server). Upon identification of a player opponent by the GGC server, the program initiates the player identification sequence and sequential play begins. This software sequence and control routine occurs at each remote site where play has been initiated. During the game play sequences, the program generates the appropriate animation, display, and audio data and commands, and communicates with the associated display and speaker devices. Upon the occurrence of a local player event, the main operating program displays the event and communicates the event by causing a device transmission to be sent via the internet GGC server which displays the event for the opposing players and alerts an opposing player that it is his/her turn to play. The local player event may be, but is not limited to the smart sports equipment impacting a ball, for example the swing of a golf club across the sensing plate or the balls entry into the receptacle. The program contains time delay limits for player action, and delays of play beyond these limits generate play quit and disconnect signals.

The event at also has the effect of indicating at that it is no longer the local player's turn and enables the socket event listener to detect an event from the remote player, again via the Internet.

If the single player practice mode is selected, the internet communications sequences are disabled, other software sequential operating routines continue as above described and the player's movement, ball-receptacle contact, and/or motion sensor information are communicated only to the computer located at the player's site and the performance information analyzed and displayed only at the local player's site.

When a game is won, lost, or terminated, the software system generates the appropriate output signals, displays the player performance information, and resets to initial pre-game conditions. If one player opponent quits the game or is "timed out" (due to excessive delay in play) and the remaining player wishes to continue play, the software resumes an Internet search for another opponent.

The motion sensing device contains a wireless processor which detects and distinguishes various wireless protocols, for example Bluetooth, Zigbee, or Wi-Fi, from each other. The wireless processor allows the present invention to use embedded single and multiplayer software to communicate and exchange information with original and cloned devices embodying the present invention.

The wireless processor has the ability to memorize whatever wireless protocol it last read to display information. The display is capable of showing animations specific to the wireless protocol.

A physiological processor and the sound processor work in similar fashion.

The physiological processor wirelessly cures and processes heart rate, respiration rate and brain waves, using a variety of well-known and established technologies. Among these technologies are the electroencephalogram for measuring brain waves to tell the differences between the alpha and beta states whereby sensors are attached to the head area. Heart rates are measured by electrocardiogram. Often times pulse readings are measured to determine heart rate by attaching an electrode to a finger tip or ear lobe. Respiration rates are sometimes measured by a Piezoelectric respiration sensor, which is worn around the chest area. All three measurements for heart rate, brain waves and respiration rates are sent to the physiological processor wirelessly for analysis and processing. The embedded single and multiplayer software allows the physiological processor to exchange messages and data with other original and cloned sports apparatus and other internet sports computer cellular devices off and on the Internet using client server and peer to peer network.

The sound processor captures, analyzes, stores, plays back and synchronizes a quality of movement particular sounds to inform a user of said quality.

Another embodiment of the present invention makes use of infrared markers or light emitting diodes. In said embodiment, the marker is a five-sided facet. The side facets slope from the main facet at an angle between 10 to 15 degrees in reference to the front side of the facet. The LED device emits light upon activation of the same by a typical power supply, which may be a battery or other device. The power supply is also secured to the body of the user by conventional techniques. One can analyze the motion of an arm, a back and other body parts and develop the three dimensional X, Y, and Z coordinate information for various body parts. For example, to measure the angle between the hip joint, one would know said coordinates at the knee joint with relation to the hip.

Using programming as contained in the accompanying microfiche appendix of the parent application, one skilled in the art can readily accomplish the game programming described. Alternative programming too will be apparent from the foregoing functional description and the illustrations contained in the appended drawings.

A sports gaming, handheld device wherein the handheld device opens into two halves.

One half of the open handheld device comprises a plurality of buttons wherein said buttons are flat so that the handheld device can close completely. One half of the open handheld device comprises at least one camera capable of encoding digital images and videos digitally storing images and videos and stabilizing images and videos. The sports gaming, handheld device further comprises a plurality of processors that measure and store physiological data, device specific data and user motion data in real-time, with at least one processor capable of transmitting physiological real-time data, device real-time data and user motion real-time data to at least one electronic console at least one processor capable of transmitting videos and digital images in real-time to at least one electronic console. At least one processor is capable of receiving real-time data from at least one electronic console. At least one processor has built-in global positioning system capability. At least one processor is capable of transmitting motion data to a monitor display. In an embodiment, the plurality of processors are comprising sensors that are attached wirelessly to the user, a central processing unit, a processor capable of storing general data, a processor capable of storing user physiological data and motion data, a processor capable of receiving wireless transmissions, a processor capable of detecting, storing, and receiving user data, a processor capable of determining strength of wireless connectivity and choosing the strongest connection, a processor capable of connecting to at least one cellular device, a processor capable of password and informational storage, a processor capable of comparing data from differing users, a processor capable of monitoring physiological data, a processor capable of monitoring motion data wherein motion data relates to sports actions performed by the user, a processor capable of monitoring handheld device specific data.

In another embodiment, the plurality of processors transmit and receive aforementioned real-time data to and from the at least one electronic console via at least one of RFID, Zigbee, Bluetooth, Wi-Fi, Wi-Max, a local area network and cellular router.

In another embodiment, the plurality of processors comprises a processor capable of receiving transmissions from the at least one electronic console wherein said transmission produces sound feedback related to at least one of the physiological real-time data, device real-time data and user motion real-time data, said sound feedback comprises at least one of: voice feedback, pre-programed feedback, audio downloads, satellite radio, Dolby sound, and Yamaha sound. Additionally, the embodiment comprises a processor capable of gathering physiological real-time and stored data and motion real-time and stored data and comparing it to stored data on the at least one electronic console, said processor transmits differences from real-time and stored user data and stored data to the at least one electronic console.

In another embodiment, the stored data on the electronic console is physiological and motion data from professional athletes. The physiological data stored may comprise heart rate measurements, respiration rate measurements, and brain waive activity measurements, among others. The device may also be capable of receiving and transmitting phone calls.

A method for a sports gaming, handheld device comprises providing the systems discussed herein, wherein a handheld device automatically detects wireless networks and automatically connects to a detected frequency. In another embodiment of the method, a set of preferences can be used to connect to a preferred wireless network. The processors may detect at least one of the following frequencies: Zigbee, Bluetooth, rf, wi-fi, wi-max, uwb, local area network and cellular router.

The method may be further comprising the steps of gathering of physiological data by at least one processor, selecting specific physiological data by the at least one processor, transmission of selected physiological data to a second at least one processor, further selecting specific physiological data, transmission of selected physiological data to a third at least one processor, filtering of specific physiological data, transmission of physiological data to at least one electronic console storage of physiological data, comparison of user physiological data with previously stored physiological data.

In another embodiment, the physiological data is at least one of heart-rate data, respiration data and brain wave data. The previously stored physiological data may be physiological data relating to professional athletes. The motion of the user may be compared directly to the motion of the stored professional athletes, and a comparison to said physiological data may result in visual and sound feedback relating to the user data.

While preferred embodiments have been described, it will be appreciated that many variations and modifications in the system, its operation, and its various components may be made without departure from the spirit and scope of invention as set forth in the appended claims.

What is claimed is:

1. A system including a first sports device, a second sports device, and a third sports device, each sports device connected to a network of sports devices,
   the first sports device comprising a first sports apparatus, a first display screen, a first digital camera, a first processor, a first set of one or more motion sensors, a first set of one or more physiological sensors, a first GPS apparatus, a first speaker, a first microphone, a first power supply, the first sports device being operated by a first user in a first location;
   the second sports device comprising a second sports apparatus, a second display screen, a second digital camera, a second processor, a second set of one or more motion sensors, a second set of one or more physiological sensors, a second GPS apparatus, a second speaker, a second microphone, a second power supply, the second sports device being operated by a second user in a second location;
   the third sports device comprising a third sports apparatus, a third display screen, a third digital camera, a third processor, a third set of one or more motion sensors, a third set of one or more physiological sensors, a third GPS apparatus, a third speaker, a third microphone, a third power supply, the third sports device being operated by a third user in a third location;
   the first set of one or more motion sensors configured to be worn by the first user, the second set of one or more motions sensors configured to be attached to the first sports apparatus, the third set of one or more motion sensors configured to be worn by the third user or attached to the third sports apparatus;
   the first, second, and third sets of one or more motion sensors configured to capture velocity data in a non-visual format;
   the first processor in wireless communication with the first set of one or more motion sensors and the first GPS apparatus, and programmed to receive a first set of motion data from the first GPS apparatus and the first set of one or more motion sensors, the first processor configured to calculate a first numerical representation using the first set of motion data, transmit the first set of motion data to the second sports device and the third sports device, and receive a second set of motion data from the second sports device and a third set of motion data from the third sports device;
   the third processor in wireless communication with the third set of one or more motion sensors and the third GPS apparatus, and programmed to receive the third set of motion data from the third GPS apparatus and the third set of one or more motion sensors, the third processor configured to transmit the third set of motion data to the first sports device and the second sports device, and receive the first set of motion data from the first sports device and the second set of motion data from the second sports device;
   the second processor in wireless communication with the second set of one or more motion sensors and the second GPS apparatus, and programmed to receive the second set of motion data from the second GPS apparatus and the second set of one or more motion sensors, the second processor configured to transmit the second set of motion data to the first sports device and the third sports device, and receive the first set of motion data from the first sports device and the third set of motion data from the third sports device; and
   the first processor programmed to make a first calculation using the first, second, and third set of motion data.

2. The system in claim 1, the first set of one or more physiological sensors configured to be worn by the first user and including an EKG apparatus for measuring heart rate, the second set of one or more physiological sensors configured to be worn by the second user and including an EEG apparatus for measuring brain waves, the third set of one or more physiological sensors configured to be worn by the third user and including a piezoelectric respiration sensor for measuring respiration rate.

3. The system in claim 2, the first processor in wireless communication with the first set of one or more physiological sensors, programmed to receive a first set of physiological data from the first set of one or more physiological sensors, and configured to transmit the first set of physiological data to the second sports device and the third sports device and receive a second set of physiological data from the second sports device and a third set of physiological data from the third sports device;
   the third processor in wireless communication with the third set of one or more physiological sensors, programmed to receive the third set of physiological data from the third set of one or more physiological sensors, and configured to transmit the third set of physiological data to the second sports device and the first sports device and receive the second set of physiological data from the second sports device and the first set of physiological data from the first sports device;
   the second processor in wireless communication with the third set of one or more physiological sensors, programmed to receive the second set of physiological data from the second set of one or more physiological sensors, and configured to transmit the second set of physiological data to the first sports device and the third sports device and receive the first set of physiological data from the first sports device and the third set of physiological data from the third sports device; and the second processor programmed to make a second calculation using the first, second, and third set of physiological data.

4. The system in claim 1, the first processor coupled to the first speaker and the first microphone, and programmed to receive a first set of sound data from the first microphone, transmit the first set of sound data to the second sports device and the third sports device, receive a second set of sound data from the second sports device and a third set of sound data from the third sports device, and transmit the second and third set of sound data to the first speaker;

the second processor coupled to the second speaker and the second microphone, and programmed to receive the second set of sound data from the second microphone, transmit the second set of sound data to the first sports device and third sports device, receive the first set of sound data from the first sports device and the third set of sound data from the third sports device, and transmit the second and third set of sound data to the second speaker; and the third processor coupled to the third speaker and the third microphone, and programmed to receive the third set of sound data from the third microphone, transmit the third set of sound data to the first sports device and the second sports device, receive the first set of sound data from the first sports device and the second set of sound data from the second sports device, and transmit the first and second set of sound data to the third speaker.

5. A system including a first sports device, a second sports device, and a third sports device, each sports device connected to a network of sports devices, the first sports device comprising a first sports apparatus, a first display screen, a first digital camera, a first processor, a first set of one or more motion sensors, a first set of one or more physiological sensors, a first GPS apparatus, a first speaker, a first microphone, a first power supply, the first sports device being operated by a first user in a first location;

the second sports device comprising a second sports apparatus, a second display screen, a second digital camera, a second processor, a second set of one or more motion sensors, a second set of one or more physiological sensors, a second GPS apparatus, a second speaker, a second microphone, a second power supply, the second sports device being operated by a second user in a second location;

the third sports device comprising a third sports apparatus, a third display screen, a third digital camera, a third processor, a third set of one or more motion sensors, a third set of one or more physiological sensors, a third GPS apparatus, a third speaker, a third microphone, a third power supply, the third sports device being operated by a third user in a third location;

the first set of one or more physiological sensors configured to be worn by the first user and including an EKG apparatus for measuring heart rate, the second set of one or more physiological sensors configured to be worn by the second user and including an EEG apparatus for measuring brain waves, the third set of one or more physiological sensors configured to be worn by the third user and including a piezoelectric respiration sensor for measuring respiration rate;

the first processor in wireless communication with the first set of one or more physiological sensors, programmed to receive a first set of physiological data from the first set of one or more physiological sensors, and configured to transmit the first set of physiological data to the second sports device and the third sports device and receive a second set of physiological data from the second sports device and a third set of physiological data from the third sports device;

the third processor in wireless communication with the third set of one or more physiological sensors, programmed to receive the third set of physiological data from the third set of one or more physiological sensors, and configured to transmit the third set of physiological data to the second sports device and the first sports device and receive the second set of physiological data from the second sports device and the first set of physiological data from the first sports device;

the second processor in wireless communication with the third set of one or more physiological sensors, programmed to receive the second set of physiological data from the second set of one or more physiological sensors, and configured to transmit the second set of physiological data to the first sports device and the third sports device and receive the first set of physiological data from the first sports device and the third set of physiological data from the third sports device; and the second processor programmed to make a first calculation using the first, second, and third set of physiological data.

6. The system of claim 5, the first set of one or more motion sensors configured to be worn by the first user, the second set of one or more motions sensors configured to be attached to the first sports apparatus, the third set of one or more motion sensors configured to be worn by the third user or attached to the third sports apparatus;

the first, second, and third sets of one or more motion sensors configured to capture velocity data in a non-visual format;

the first processor in wireless communication with the first set of one or more motion sensors and the first GPS apparatus, and programmed to receive a first set of motion data from the first GPS apparatus and the first set of one or more motion sensors, the first processor configured to calculate a first numerical representation using the first set of motion data, transmit the first set of motion data to the second sports device and the third sports device, and receive a second set of motion data from the second sports device and a third set of motion data from the third sports device;

the third processor in wireless communication with the third set of one or more motion sensors and the third GPS apparatus, and programmed to receive the third set of motion data from the third GPS apparatus and the third set of one or more motion sensors, the third processor configured to transmit the third set of motion data to the first sports device and the second sports device, and receive the first set of motion data from the first sports device and the second set of motion data from the second sports device;

the second processor in wireless communication with the second set of one or more motion sensors and the second GPS apparatus, and programmed to receive the second set of motion data from the second GPS apparatus and the second set of one or more motion sensors, the second processor configured to transmit the second set of motion data to the first sports device and the third sports device, and receive the first set of motion data from the first sports device and the third set of motion data from the third sports device; and the first processor programmed to make a second calculation using the first, second, and third set of motion data.

7. The system in claim 5, the first processor coupled to the first speaker and the first microphone, and programmed to receive a first set of sound data from the first microphone, transmit the first set of sound data to the second sports device and the third sports device, receive a second set of sound data from the second sports device and a third set of sound data from the third sports device, and transmit the second and third set of sound data to the first speaker;
the second processor coupled to the second speaker and the second microphone, and programmed to receive the second set of sound data from the second microphone, transmit the second set of sound data to the first sports device and third sports device, receive the first set of sound data from the first sports device and the third set of sound data from the third sports device, and transmit the second and third set of sound data to the second speaker; and
the third processor coupled to the third speaker and the third microphone, and programmed to receive the third set of sound data from the third microphone, transmit the third set of sound data to the first sports device and the second sports device, receive the first set of sound data from the first sports device and the second set of sound data from the second sports device, and transmit the first and second set of sound data to the third speaker.

8. The system of claim 5, the first set of one or more physiological sensors configured to be worn by the first user on a wrist and including an EKG apparatus for measuring heart rate, the second set of one or more physiological sensors embedded in a head band and configured to be worn by the second user and including an EEG apparatus for measuring brain waves, the third set of one or more physiological sensors configured to be worn by the third user and including a piezoelectric respiration sensor for measuring respiration rate.

9. A system including a first sports device, a second sports device, and a third sports device, each sports device connected to a network of sports devices,
the first sports device comprising a first sports apparatus, a first display screen, a first digital camera, a first processor, a first set of one or more motion sensors, a first set of one or more physiological sensors, a first speaker, a first microphone, a first power supply, the first sports device being operated by a first user in a first location;
the second sports device comprising a second sports apparatus, a second display screen, a second digital camera, a second processor, a second set of one or more motion sensors, a second set of one or more physiological sensors, a second speaker, a second microphone, a second power supply, the second sports device being operated by a second user in a second location;
the third sports device comprising a third sports apparatus, a third display screen, a third digital camera, a third processor, a third set of one or more motion sensors, a third set of one or more physiological sensors, a third speaker, a third microphone, a third power supply, the third sports device being operated by a third user in a third location;
the first processor coupled to the first speaker and the first microphone, and programmed to receive a first set of sound data from the first microphone, transmit the first set of sound data to the second sports device and the third sports device, receive a second set of sound data from the second sports device and a third set of sound data from the third sports device, and transmit the second and third set of sound data to the first speaker;
the second processor coupled to the second speaker and the second microphone, and programmed to receive the second set of sound data from the second microphone, transmit the second set of sound data to the first sports device and third sports device, receive the first set of sound data from the first sports device and the third set of sound data from the third sports device, and transmit the second and third set of sound data to the second speaker; and
the third processor coupled to the third speaker and the third microphone, and programmed to receive the third set of sound data from the third microphone, transmit the third set of sound data to the first sports device and the second sports device, receive the first set of sound data from the first sports device and the second set of sound data from the second sports device, and transmit the first and second set of sound data to the third speaker;
the system of claim 8, the first sports device comprising a first GPS apparatus the second sports device comprising a second GPS apparatus, the third sports device comprising a third GPS apparatus;
the first set of one or more motion sensors configured to be worn by the first user, the second set of one or more motions sensors configured to be attached to the first sports apparatus, the third set of one or more motion sensors configured to be worn by the third user or attached to the third sports apparatus;
the first, second, and third sets of one or more motion sensors configured to capture velocity data in a non-visual format and without the use of the first, second, or third GPS apparatus;
the first processor in wireless communication with the first set of one or more motion sensors and the first GPS apparatus, and programmed to receive a first set of motion data from the first GPS apparatus and the first set of one or more motion sensors, the first processor configured to calculate a first numerical representation using the first set of motion data, transmit the first set of motion data to the second sports device and the third sports device, and receive a second set of motion data from the second sports device and a third set of motion data from the third sports device;
the third processor in wireless communication with the third set of one or more motion sensors and the third GPS apparatus, and programmed to receive the third set of motion data from the third GPS apparatus and the third set of one or more motion sensors, the third processor configured to transmit the third set of motion data to the first sports device and the second sports device, and receive the first set of motion data from the first sports device and the second set of motion data from the second sports device;
the second processor in wireless communication with the second set of one or more motion sensors and the second GPS apparatus, and programmed to receive the second set of motion data from the second GPS apparatus and the second set of one or more motion sensors, the second processor configured to transmit the second set of motion data to the first sports device and the third sports device, and receive the first set of motion data from the first sports device and the third set of motion data from the third sports device; and the first processor programmed to make a first calculation using the first, second, and third set of motion data.

10. The system of claim 9, the first set of one or more physiological sensors configured to be worn by the first user and including an EKG apparatus for measuring heart rate, the second set of one or more physiological sensors configured to be worn by the second user and including an EEG apparatus for measuring brain waves, the third set of one or more physiological sensors configured to be worn by the third user and including a piezoelectric respiration sensor for measuring respiration rate;

the first processor in wireless communication with the first set of one or more physiological sensors, programmed to receive a first set of physiological data from the first set of one or more physiological sensors, and configured to transmit the first set of physiological data to the second sports device and the third sports device and receive a second set of physiological data from the second sports device and a third set of physiological data from the third sports device;

the third processor in wireless communication with the third set of one or more physiological sensors, programmed to receive the third set of physiological data from the third set of one or more physiological sensors, and configured to transmit the third set of physiological data to the second sports device and the first sports device and receive the second set of physiological data from the second sports device and the first set of physiological data from the first sports device;

the second processor in wireless communication with the third set of one or more physiological sensors, programmed to receive the second set of physiological data from the second set of one or more physiological sensors, and configured to transmit the second set of physiological data to the first sports device and the third sports device and receive the first set of physiological data from the first sports device and the third set of physiological data from the third sports device; and the second processor programmed to make a second calculation using the first, second, and third set of physiological data.

11. The system of claim 10, the first processor programmed to convert the first set of physiological data into a first set of graphic physiological data, display the first set of graphic physiological data on a first graphical portion of the first display screen, convert the first set of motion data into a first set of graphic motion data, and display the first set of graphic motion data on a second graphical portion of the first display screen.

12. The system of claim 10, the second processor programmed to convert the first and third set of physiological data into a second set of graphic physiological data, display the second set of graphic physiological data on a first graphical portion of the second display screen, convert the first and third set of motion data into a second set of graphic motion data, and display the second set of graphic motion data on a second graphical portion of the second display screen.

13. The system of claim 10, the third processor programmed to convert the first and second set of physiological data into a third set of graphic physiological data, display the third set of graphic physiological data on a first graphical portion of the third display screen, convert the third set of physiological data into a fourth set of graphic physiological data, display the fourth set of graphic physiological data on a second graphical portion of the third display screen, convert the first and second set of motion data into a third set of graphic motion data, display the third set of graphic motion data on a third graphical portion of the third display screen, convert the third set of motion data into a fourth set of graphic motion data, and display the fourth set of graphic motion data on a fourth graphical portion of the third display screen.

* * * * *